United States Patent [19]

Miller et al.

[11] Patent Number: 5,008,244
[45] Date of Patent: Apr. 16, 1991

[54] METHOD FOR INCREASING FERTILITY IN ANIMALS

[75] Inventors: Lindy F. Miller, West Terre Haute; Peter J. Thomford, Terre Haute, both of Ind.

[73] Assignee: Pitman-Moore, Inc., Lake Forest, Ill.

[21] Appl. No.: 352,010

[22] Filed: May 15, 1989

[51] Int. Cl.$^5$ .............................................. A61K 37/02
[52] U.S. Cl. ....................................... 514/12; 514/21; 514/806
[58] Field of Search ............................ 514/12, 21, 806

[56] References Cited

U.S. PATENT DOCUMENTS 4,061,737 12/1977 Alburn et al. ........................ 424/177
4,521,409 6/1985 Bauman et al. ....................... 514/21

OTHER PUBLICATIONS

C.A. 110:1208(a) Phillips, The Use of Prolonged Release Bovine Somatotropin in Milk Production, 1989.
Bryan et al., *Reproductive and Growth Responses of Gilts to Exogenous Porcine Pituitary Growth Hormone*, Journal of Animal Science, vol. 67, No. 1, pp. 196–205 (1989).

Primary Examiner—Lester L. Lee
Attorney, Agent, or Firm—Wendell Ray Guffey; Thomas L. Farquer

[57] ABSTRACT

Somatotropin is administered to food producing animals in the finishing stage of growth to increase fertility by increasing embryonic survival and litter size during the reproductive stage of growth.

20 Claims, No Drawings

METHOD FOR INCREASING FERTILITY IN ANIMALS

This invention relates generally to methods for increasing fertility in animals and particularly to a method for increasing fertility in food producing animals by administering somatotropin to the animals in the finishing phase of growth to increase embryonic survival and litter size during the reproductive stage of growth.

BACKGROUND OF THE INVENTION

1. Somatotropin

The isolation, purification and properties of somatotropins are well known in the art. Generally, somatotropin, sometimes referred to as growth hormone in the art, is produced by the pituitary throughout an animal's life, although apparently in higher amounts during the pre-adult period. Somatotropin is known to promote skeletal growth, nitrogen retention, protein synthesis and to affect glucose and lipid metabolism. Accordingly, somatotropin is recognized as a general anabolic agent.

Somatotropin can be isolated from excised pituitary tissue. See, e.g., C. H. Li, *J. Biol. Chem.* 211, 55 (1954). Somatotropin can also be obtained from genetically engineered microorganisms containing recombinant DNA which specifies the production of somatotropin. See, e.g., P. H. Seeburg, et al., *Nature*, 276, 795–798 (1978); P. H. Seeburg et al., *Nature*, 270, 486–494 (1978); J. A. Martial, *Science*, 205, 602–607 (1979).

Somatotropins from particular species have been studied and characterized. For example, bovine somatotropin (bST) is known to be a polypeptide synthesized in and secreted from the anterior lobe of the pituitary. A nucleotide coding sequence and an amino acid sequence of native bovine somatotropin have been reported; e.g. W. L. Miller et al., *J. Biol. Chem.*, 255, 7521–24 (1980); M. D. Dayhoff et al., in "Atlas of Protein Sequence And Structure", Dayhoff ed., 5, Supp. 3, 345–42 (1978); and M. Wallis, *FEBS Lett*, 35, 11–14 (1973). Bovine somatotropin is a protein of 191 amino acids and appears to be synthesized initially as a bovine pre-somatotropin of 217 amino acids; the signal sequence of 26 amino acids being removed from the N-terminal position during synthesis and secretion, e.g. V. R. Lingapa et al., *Proc. Natl. Acad. Sci. USA*, 74, 2432–36 (1977).

The preparation of bovine somatotropin is well known in the art. For example, bovine somatotropin is extracted from pituitary glands of cattle or produced via recombinant DNA technology in appropriate hosts, e.g., W. L. Miller et al., *J. Biol. Chem.*, 255, 7521–24 (1980). U.S. Pat. No. 4,443,539 to Frazier et al, discloses a process for preparing bovine somatotropin by utilizing recombinant DNA methodology to place the bovine somatotropin structural gene into yeast cells. U.S. Pat. No. 4,371,462 to Hecht, discloses a method for the purification of anterior pituitary peptides. European Patent Application Nos. 83304574.3, filed Aug. 8, 1983, with Publication Number 103,395; 82304880.6, filed Sept. 16, 1982, with Publication Number 075,444; and 81303824.7, filed Aug. 21, 1981, with Publication Number 047,600; and British Patent Application No. 2,073,245A disclose methods for producing recombinant bovine somatotropin in high yields. Strains of *E. coli* that produce bovine somatotropin are available from the American Type Culture Collection under accession numbers ATCC 31826, 31840, 31841, 31842, and 31843.

Similarly, the preparation of natural and recombinant porcine and human somatotropin is well known. For example, in addition to the publications above which disclose methods for obtaining the porcine and human somatotropin, U.S. Pat. No. 4,604,359 discloses methods for the microbial expression of human somatotropin; U.S. Pat. No. 4,332,717 discloses methods for the purification of human somatotropin; and European Patent Application No. 83305717.7, filed Sept. 26, 1983, with Publication Number 104,920, discloses methods for producing recombinant porcine somatotropin in high yields. Many other such publications and methods are well known to skilled artisans.

2. Fertility

The success and profit for animal breeders raising cattle, swine, sheep, and many other animals depends largely upon the ability to produce large numbers of viable offspring. It is, therefore, desirable to increase the birth rate by insuring that a larger percentage of fertilized eggs mature into viable offspring. In the natural method, allowing two animals to mate, the egg may be fertilized but the embryo may not survive. Often multiple births may be rare or litters may be smaller than desirable because all the fertilized eggs that develop into embryos may not survive to produce viable offspring.

Various methods have been developed to overcome these problems. Methods for increasing fertility in animals by stimulating and controlling ovulation have increased the conception rate. Treating animals with progesterone and other steroidal compounds can significantly increase the conception rate, but the high cost of steroidal products and the adverse side effects have prevented their widespread use. For example, U.S. Pat. Nos. 3,830,907 and 3,565,991 disclose using nortesterone compounds to control ovulation and estrus. Numerous patents, e.g. U.S. Pat. Nos. 2,379,832, 2,232,438, and 2,324,185, have related to progesterone which has been used to control habitual abortion and suppress or synchronize estrus. These compounds, however, are often expensive, difficult to handle, and have adverse side effects such as estrogenic-like changes in body weight, uterine weight, etc. in the animal.

Other compounds have also been used to increase fertility by controlling and stimulating ovulation. U.S. Pat. No. 4,283,419 discloses administering tris-(2-ethoxy-ammonium- orthocresoxy) acetate and U.S. Pat. No. 3,463,860 discloses administering para-hydroxybenzoic acid esters to increase fertility in animals. Japanese Patent 58043725 discloses feeding arginine and lysine to cattle to increase birth rate from approximately 50% to 83.3%. These compounds, however, generally have estrogen-type side effects characteristic of the analogous hormonal compounds.

An effective method is, therefore, needed which can increase fertility in animals, particularly food producing animals, by increasing embryonic survival and litter size without producing the adverse side effects characteristic of prior methods for increasing fertility.

SUMMARY OF THE INVENTION

It is, therefore, an object of the present invention to increase fertility in food producing animals which are in the reproductive stage of growth.

It is another object of the present invention to increase the embryonic survival rate in food producing animals which are in the reproductive stage of growth.

It is another object of the present invention to increase litter size in food producing animals which are in the reproductive stage of growth.

These and other objects are achieved by administering a fertility increasing amount of somatotropin to a food producing animal selected from the bovine, porcine or ovine species in the finishing stage of growth. Somatotropin, administered in the proper dosage and with the proper timing during the finishing stage of growth, has several desirable and beneficial effects that become evident during the reproductive stage of growth; the embryonic survival rate is increased thereby optimizing the number of offspring produced and the litter size is increased thereby producing more offspring per pregnancy. Somatotropin lacks the undesirable estrogenic activity characteristic of some previous compounds but has the fertility increasing properties characteristic of prior art compounds.

In the preferred embodiment, somatotropin is administered to a food producing animal in the finishing stage of growth in dosages from about 0.1-20 mg/animal/day, preferably from about 3-12 mg/animal/day, to increase fertility by increasing embryonic survival and litter sizes during the reproductive stage of growth.

In the most preferred embodiment, porcine somatotropin is administered to swine in the finishing stage of growth in dosages from about 0.1-20 mg/animal/day, preferably from about 3-12 mg/animal/day, to increase fertility by increasing embryonic survival and litter sizes during the reproductive stage of growth.

Other objects, advantages, and novel features of the present invention will become apparent from the following detailed description of the invention.

DETAILED DESCRIPTION OF THE INVENTION

The term "food producing animal" is defined herein to mean an animal from the bovine, porcine or ovine species.

The term "finishing" is defined herein to mean the stage of growth in a food producing animal just prior to the reproductive or market stage of growth. For example, for porcine species, the growth stages are approximately as follows: (1) "suckling"—the stage of growth when the animal is relying on the mother's milk for food, typically until about 21 days of age when the animal is weaned; (2) "nursery"—the stage of growth from weaning until about 56 days of age, the animal is usually kept in a controlled environment and on a special diet; (3) "grower"—the stage of growth from about 56 to about 110 days of age or until the animal has reached about 100 pounds or 50 kilograms of weight, the animal is usually kept in a somewhat controlled environment and fed a high protein swine diet; (4) "finishing"—the stage of growth from about 110 to about 165 days of age or until the animal has reached about 200 pounds or 100 kilograms of weight, the animal is usually kept in a open pen and fed a traditional swine diet; (5) "market" or "reproductive"—the stage of growth after finishing when the animal is marketed or retained in the breeding herd. The growth stages are similar for bovine and ovine species; such growth stages are known to skilled artisans.

According to the present invention, somatotropin is administered to food producing animals selected from the bovine, porcine or ovine species in the finishing stage of growth in amounts sufficient to increase fertility by increasing embryonic survival and litter sizes during the reproductive stage of growth. Somatotropin apparently does not increase the fertility of animals if administered in other stages of growth or development, Bryan et al., Reproductive and Growth Responses of Gilts to Exogenous Porcine Pituitary Growth Hormone, *J. Anim. Sci.* 1989: 67:196–205.

Somatotropins used herein can be obtained from any suitable source. Methods for producing, isolating and purifying native and recombinant somatotropin are well known in the field. Somatotropin as used herein includes all proteins having somatotropin activity including natural, recombinant, mutein and analog proteins having deleted, replaced, or otherwise altered amino acid sequences. Somatotropin as used herein also includes the protein's biologically active and pharmaceutically acceptable salts, esters and other derivatives. In particular, somatotropins used herein include recombinant proteins of the same sequence as the native somatotropin, but having amino acids deleted from the amino and/or carboxy terminal end. Examples of such proteins include but are not limited to delta-7 recombinant porcine somatotropin, delta-4 recombinant bovine somatotropin, (native somatotropins having 7 and 4 residues deleted from the amino terminal end, respectively), and the like.

Several recombinant somatotropins are known in the art. European Patent Application Publication No. 0 103 395 describes the construction of a transformant strain of *E. coli* containing a first plasmid which codes for delta-9 (Ser) bovine somatotropin (somatotropin less its 9 N-terminal amino acids and having an additional serine residue at the N-terminus) under the control of the lambda P L promoter-operator and which has a Shine-Dalgarno region derived from bacteriophage mu. The transformant also contains a second plasmid, pcI857, which codes for the production of the pcI857 temperature-sensitive repressor protein. The repressor protein can be inactivated by raising the temperature to about 42° C., thereby inducing expression of delta-9 (Ser) bovine somatotropin. A transformant strain of this type, *E. coli* HB101 (P L-mu-delta-9 (Ser) bovine somatotropin and pcI857) has been deposited, with The American Type Culture Collection (ATCC), Rockville, Md. and assigned Accession No. 53030.

Construction of a similar transformant strain which codes for the production of delta-7 porcine somatotropin (porcine somatotropin less its first 7 N-terminal amino acids) is described in European Patent Application Publication No. 0 104 920. A transformant strain of this type, *E. coli* HB101 (P L-mu-delta-7 porcine somatotropin and pcI857) has been deposited with ATCC and assigned Accession No. 53031.

Strains 53030 and 53031 are prolific producers of delta-9 (Ser) bovine somatotropin and delta-7 porcine somatotropin, respectively. Other methods for many similar proteins are known in the art.

Somatotropin according to the present invention can be administered to the animal in any acceptable manner including by injection, using an implant, and the like. Injections are preferred because they permit precise control of the timing and dosage levels used for administration. Somatotropins according to the present invention are preferably administered parenterally. As used herein, parenteral administration means by intravenous, intramuscular, subcutaneous or intraperitoneal injection, or by subcutaneous implant.

When administered by injection, somatotropin according to the present invention can be administered to the animal in an injectable formulation containing any biocompatible and somatotropin compatible carrier such as various vehicles, adjuvants, additives, and diluents. Somatotropin according to the present invention is added to the carrier in amounts sufficient to supply from about 0.1-20 mg/animal/day to the animal when injected. In one preferred embodiment, somatotropin according to the present invention is added to a buffer containing about 300 mg/ml arginine hydrochloride and about 0.9% benzyl alcohol in amounts sufficient to supply from about 3-12 mg/animal/day Many other such vehicles are known to those skilled in the art. For example, U.S. Pat. No. 4,637,834, incorporated herein by reference, discloses compounds useful as additives for macromolecular proteins. A preferred vehicle (buffer) containing such additives comprises the somatotropin, 0.2M Tris, 2 mM EDTA, and 0.15% BRIJ 35.

Aqueous vehicles prepared from water having no nonvolatile pyrogens, sterile water, and bacteriostatic water and containing at least 0.025M buffer salts, such as sodium phosphate, sodium bicarbonate, sodium citrate, etc. are also suitable to form injectable somatotropin solutions. In addition to these buffers, several other aqueous vehicles can be used. These include isotonic injection compositions that can be sterilized such as sodium chloride, Ringer's, dextrose, dextrose and sodium chloride, and lactated Ringer's. Addition of water-miscible solvents, such as methanol, ethanol, or propylene glycol generally increases solubility and stability of somatotropin in these vehicles.

Nonaqueous vehicles such as cottonseed oil, sesame oil, or peanut oil and esters such as isopropyl myristate may also be used as suspension vehicles for somatotropin compositions. Additionally, various additives which enhance the stability, sterility and isotonicity of the composition including antimicrobial preservatives, antioxidants, chelating agents, and buffers can be added. Any vehicle, diluent, or additive used would, however, have to be biocompatible and compatible with somatotropin according to the present invention.

Somatotropin according to the present invention can be administered to the animal in the form of a slow-release subcutaneous implant which is inserted beneath the skin of the animal. The implant can take the form of a pellet which slowly dissolves after being implanted in the animal or a biocompatible delivery module well known to those skilled in the art. Such well known dosage forms are designed such that the active ingredients are slowly released over a period of several days to several weeks. The implant is designed to deliver from about 0.1-20 mg/animal/day.

Although not preferred because the digestive system tends to inactivate proteins, somatotropin can be administered orally if administered in a dosage form which prevents inactivation of the compounds by the digestive system. Such techniques and dosage forms are well known in the art; U.S. Pat. No. 4,639,435 to Fujii et al. discloses pharmaceutical compositions designed to deliver protein compounds orally without significant loss of bioactivity usually associated with oral administration.

The somatotropins herein are administered to animals of the same species; i.e. porcine somatotropin is administered to the porcine species, bovine somatotropin is administered to the bovine species, and ovine somatotropin is administered to the ovine species.

Although the dosages of somatotropin vary according to the type of animal, age of the animal, size of the animal, and the like, somatotropin is typically administered to the animal in dosages from about 0.1-20 mg/animal/day, preferably from about 3-12 mg/animal/day, to increase fertility by increasing embryonic survival and litter size during the reproductive stage of growth.

In the most preferred embodiment of the present invention, porcine somatotropin is administered to finishing swine in amounts sufficient to increase fertility by increasing embryonic survival and litter sizes during the reproductive stage of growth. Most preferably, delta-7 porcine somatotropin is administered in amounts of from about 0.1-20 mg/animal/day, preferably from about 3-12 mg/animal/day, to increase fertility by increasing embryonic survival and litter size during the reproductive stage of growth.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

Forty crossbred gilts, including 19 littermate pairs, were assigned to the study at an average body weight of 50 kg. An equal number of these gilts were randomly assigned within weight groups and litter number to control and delta-7 recombinant porcine somatotropin (rpST) treatment groups. Control gilts received daily intramuscular injections of 1 ml of vehicle (300 mg/ml arginine hydrochloride; 0.9% benzyl alcohol) and rpST gilts were injected daily with 1 ml of vehicle containing 6 mg of rpST. The gilts were fed ad libitum a corn-soybean ration containing 18% protein and 1.2% lysine in a confinement facility. Gilts were located in five adjacent pens with four control and four treated gilts assigned to each pen. Treatment was continued until the pen average body weight reached 110 kg. At the end of the trial the gilts were moved to a confinement gestation unit and daily heat checks made with a mature boar to determine age at puberty. Gilts were bred at second estrus with embryo recovery made at day eleven of pregnancy to determine ovulation rate, conception rate, and embryonic survival rate. The average age of all gilts at initiation of rpST treatment was 102 days with last injection given at an average age of 162 days for a total treatment period of 60 days. The results are shown in Table 1.

Referring to Table 1 for a summary of the influence of rpST on number of corpora lutea, number of embryos recovered day 11 of pregnancy, and embryonic survival rate, the data indicate an enhanced fertility through increased embryos and embryonic survival rate of rpST treated gilts. The increased embryos and embryonic survival rate produces an increased litter size.

Obviously many modifications and variations of the present invention are possible in light of the above teachings. It is, therefore, to be understood that within the scope of the appended claims the invention may be practiced otherwise than as specifically described.

TABLE 1

Effect of rpST on Embryo Survival

| Treatment | No. of gilts Bred | No. of gilts Preg. | No. of corpora lutea* | No. of embryos recovered day 11 of pregnancy* | Embryonic survival rate, % |
|---|---|---|---|---|---|
| Control | 19 | 19 | 14.3 ± 0.6 | 10.9 ± 1.0 | 76.2 |
| rpST | 19 | 19 | 14.9 ± 0.6 | 13.1 ± 0.9 | 87.9 |

*Least Squares Means ± Standard Error from Analysis of Variance.

What is claimed is:

1. A method for increasing fertility in a food producing animal selected from the bovine, porcine or ovine species, comprising:
    administering a fertility increasing amount of somatotropin to said animal in the finishing stage of growth thereby increasing embryonic survival and litter size during the reproductive stage of growth.

2. The method of claim 1 wherein said somatotropin is administered in amounts of from about 0.1–20 mg/animal/day.

3. The method of claim 1 wherein said animal is from the porcine species.

4. The method of claim 1 wherein said somatotropin is administered parenterally.

5. The method of claim 4 wherein said somatotropin is administered using an implant, said implant comprising:
    a biocompatible and somatotropin compatible implant material; and
    a fertility increasing amount of said somatotropin.

6. The method of claim 4 wherein said somatotropin is administered in an injectable formulation, said injectable formulation comprising:
    a biocompatible and somatotropin compatible carrier; and
    a fertility increasing amount of said somatotropin.

7. The method of claim 5 wherein said carrier is a buffer containing about 300 mg/ml arginine hydrochloride and about 0.9% benzyl alcohol.

8. The method of claim 1 wherein said somatotropin is a recombinant somatotropin.

9. The method of claim 8 wherein said somatotropin is delta-7 recombinant porcine somatotropin or delta-9 recombinant bovine somatotropin.

10. The method of claim 3 wherein said somatotropin is delta-7 recombinant porcine somatotropin.

11. A method for increasing fertility in a swine, comprising:
    administering a fertility increasing amount of porcine somatotropin to said swine in the finishing stage of growth thereby increasing embryonic survival and litter size during the reproductive stage of growth.

12. The method of claim 11 wherein said somatotropin is administered in amounts of from about 0.1–20 mg/swine/day.

13. The method of claim 11 wherein said somatotropin is administered parenterally.

14. The method of claim 13 wherein said somatotropin is administered using an implant, said implant comprising:
    a biocompatible and somatotropin compatible implant material; and
    a fertility increasing amount of said somatotropin.

15. The method of claim 13 wherein said somatotropin is administered in an injectable formulation, said injectable formulation comprising:
    a biocompatible and somatotropin compatible carrier; and
    a fertility increasing amount of said somatotropin.

16. The method of claim 15 wherein said carrier is a buffer containing about 300 mg/ml arginine hydrochloride and about 0.9% benzyl alcohol.

17. The method of claim 11 wherein said somatotropin is a recombinant somatotropin.

18. The method of claim 17 wherein said somatotropin is delta-7 recombinant porcine somatotropin.

19. The method of claim 11 wherein said somatotropin is administered in amounts of from about 3–12 mg/swine/day.

20. A method for increasing fertility in a swine, comprising:
    administering from about 0.1–20 mg/swine/day of delta-7 recombinant porcine somatotropin to said swine in the finishing stage of growth thereby increasing embryonic survival and litter size during the reproductive stage of growth.

* * * * *